United States Patent [19]
Chen et al.

[11] Patent Number: 5,902,598
[45] Date of Patent: May 11, 1999

[54] SUSTAINED RELEASE DRUG DELIVERY DEVICES

[75] Inventors: Jianbing Chen, Belmont; Paul Ashton, Boston, both of Mass.

[73] Assignee: Control Delivery Systems, Inc., Watertown, Mass.

[21] Appl. No.: 08/919,221

[22] Filed: Aug. 28, 1997

[51] Int. Cl.$^6$ ........................................................ A61K 9/22

[52] U.S. Cl. ..................... 424/423; 424/422; 424/424; 424/427; 424/468; 424/425; 604/890.1; 604/891.1; 604/892.1

[58] Field of Search ........................... 424/422, 423, 424/424, 425, 427; 604/890.1, 891.1, 892.1

[56] References Cited

U.S. PATENT DOCUMENTS

| | | |
|---|---|---|
| 3,416,530 | 12/1968 | Ness . |
| 3,618,604 | 11/1971 | Ness . |
| 3,630,200 | 12/1971 | Higuchi . |
| 3,632,739 | 1/1972 | Kornblum . |
| 3,896,819 | 7/1975 | Zaffaroni et al. . |
| 3,916,899 | 11/1975 | Theeuwes et al. . |
| 3,961,628 | 6/1976 | Arnold . |
| 3,977,404 | 8/1976 | Theeuwes . |
| 3,980,463 | 9/1976 | Muramoto et al. . |
| 3,993,071 | 11/1976 | Higuchi et al. . |
| 4,008,719 | 2/1977 | Theeuwes et al. . |
| 4,014,334 | 3/1977 | Theeuwes et al. . |
| 4,014,335 | 3/1977 | Arnold . |
| 4,034,758 | 7/1977 | Theeuwes . |
| 4,036,227 | 7/1977 | Zaffaroni et al. . |
| 4,077,407 | 3/1978 | Theeuwes et al. . |
| 4,111,201 | 9/1978 | Theeuwes . |
| 4,111,203 | 9/1978 | Theeuwes . |
| 4,135,514 | 1/1979 | Zaffaroni et al. . |
| 4,142,526 | 3/1979 | Zaffaroni et al. . |
| 4,186,184 | 1/1980 | Zaffaroni . |
| 4,200,098 | 4/1980 | Ayer et al. . |
| 4,247,498 | 1/1981 | Castro . |
| 4,256,108 | 3/1981 | Theeuwes . |
| 4,290,426 | 9/1981 | Luschen et al. . |

(List continued on next page.)

FOREIGN PATENT DOCUMENTS

| | | |
|---|---|---|
| 0 147 780 | 7/1985 | European Pat. Off. . |
| 180 708 | 6/1986 | European Pat. Off. . |
| 0 316 838 | 5/1989 | European Pat. Off. . |

(List continued on next page.)

OTHER PUBLICATIONS

Database WPI, Week 7943, Derwent Publications Ltd., London, GB; AN 79–78139b XP002065720 & JP 54 119 021 (Nippon Kayaku KK), Sep. 14, 1979.

Blandford et al., 5–Fluorouracil Sustained Release Device Implantation: Toxicology and Histology in Rabbits, Invest. Opthal. And Vis. Sci. 31(4):591, abstr. 2893–89 (1990).

(List continued on next page.)

*Primary Examiner*—Thurman K. Page
*Assistant Examiner*—Brian K. Seidleck
*Attorney, Agent, or Firm*—Burns, Doane, Swecker & Mathis, L.L.P.

[57] ABSTRACT

A method and device for treating a mammalian organism to obtain a desired local or systemic physiological or pharmacological effect is provided. The method includes administering a sustained release drug delivery system to a mammalian organism in need of such treatment at an area wherein release of an effective agent is desired and allowing the effective agent to pass through the device in a controlled manner. The device includes an inner core or reservoir comprising the effective agent; a first coating layer, which is permeable to the passage of the effective agent; a second coating layer, which is essentially impermeable to the passage of the effective agent; and a third coating layer, which is permeable to the passage of the effective agent. The first coating layer covers at least a portion of the inner core. The second coating layer covers at least a portion of the first coating layer and inner core; however, at least a small portion of the first coating layer or inner core is not coated with the second coating layer. The second coating layer includes an impermeable film and at least one impermeable disc. The third coating layer essentially completely covers the second coating layer and the uncoated portion of the first coating layer or inner core.

28 Claims, 2 Drawing Sheets

U.S. PATENT DOCUMENTS

| | | |
|---|---|---|
| 4,326,525 | 4/1982 | Swanson et al. . |
| 4,327,725 | 5/1982 | Cortese et al. . |
| 4,439,196 | 3/1984 | Higuchi . |
| 4,475,916 | 10/1984 | Higuchi . |
| 4,519,801 | 5/1985 | Edgren . |
| 4,519,909 | 5/1985 | Castro . |
| 4,522,625 | 6/1985 | Edgren . |
| 4,609,374 | 9/1986 | Ayer . |
| 4,615,698 | 10/1986 | Guitard et al. . |
| 4,624,847 | 11/1986 | Ayer et al. . |
| 4,627,850 | 12/1986 | Deters et al. . |
| 4,652,441 | 3/1987 | Okada et al. . |
| 4,657,543 | 4/1987 | Langer et al. . |
| 4,673,405 | 6/1987 | Guittard et al. . |
| 4,681,755 | 7/1987 | Columbo et al. . |
| 4,692,336 | 9/1987 | Eckenhoff et al. . |
| 4,693,886 | 9/1987 | Ayer . |
| 4,711,782 | 12/1987 | Okada et al. . |
| 4,716,031 | 12/1987 | Eckenhoff et al. . |
| 4,717,567 | 1/1988 | Wu et al. . |
| 4,720,384 | 1/1988 | Di Luccio et al. . |
| 4,730,013 | 3/1988 | Bondi et al. . |
| 4,777,049 | 10/1988 | Magruder et al. . |
| 4,786,500 | 11/1988 | Wong . |
| 4,806,382 | 2/1989 | Goldberg et al. . |
| 4,832,957 | 5/1989 | Dempski et al. . |
| 4,839,177 | 6/1989 | Columbo et al. . |
| 4,861,627 | 8/1989 | Mathiowitz et al. . |
| 4,865,846 | 9/1989 | Kaufman . |
| 4,877,618 | 10/1989 | Reed, Jr. . |
| 4,882,150 | 11/1989 | Kaufman . |
| 4,889,720 | 12/1989 | Konishi . |
| 4,891,223 | 1/1990 | Ambegaonkar et al. . |
| 4,898,733 | 2/1990 | DePrince et al. . |
| 4,913,906 | 4/1990 | Friedman et al. . |
| 4,927,687 | 5/1990 | Nuwayser . |
| 4,952,402 | 8/1990 | Sparks et al. . |
| 4,994,273 | 2/1991 | Aentner et al. . |
| 5,028,435 | 7/1991 | Katz et al. . |
| 5,091,185 | 2/1992 | Castillo et al. . |
| 5,098,443 | 3/1992 | Parel et al. . |
| 5,141,752 | 8/1992 | Ayer et al. . |
| 5,378,475 | 1/1995 | Smith et al. . |
| 5,435,998 | 7/1995 | Abelson . |
| 5,665,373 | 9/1997 | Robertson et al. . |

FOREIGN PATENT DOCUMENTS

| | | |
|---|---|---|
| 0 462 959 | 12/1991 | European Pat. Off. . |
| 84 00296 | 2/1984 | WIPO . |
| WO91/11176 | 8/1991 | WIPO . |
| 92 07556 | 5/1992 | WIPO . |

OTHER PUBLICATIONS

Goins et al., Intravitreal Sustained Release of Gancyclovir, Invest. Opthal. And Vis. Sci. 31(4):364, abstr. 1791 (1990).

Pearson et al., Polyvinyl Alcohol Membrane Permeability Characteristics of Gancyclovir, Invest. Opthal. And Vis. Sci. 30(4):511, abstr. 42 (1989).

Smith et al., Polyvinyl Alcohol Membrane Permeability Characteristics of 5–Fluorouracil, Journal of Ocular Pharmacology, 4(2):147–152, (1988).

Smith et al., Intraocular Sustained Release of Antiviral Agents in AIDS, Proceed. Intern. Symp. Control. Rel. Bioact. Mater. 17:470–471 (1990).

Smith et al., A Membrane Based Sustained Release Ocular Delivery System for 5–Fluorouracil, Invest. Opthal. And Vis. Sci. 30(4):271, abstr. 37 (1989).

Solomon et al., Sustained Release Drug Delivery Systems in Extracapsular Cataract Surgery, Invest. Opthal. And Vis. Sci., 31(4):351, Abstr. 1724–19 (1990).

FIG. 1

Advantages of End Discs

For clarity only the second (impermeable) coating film is shown

SUSTAINED RELEASE DRUG DELIVERY DEVICES

FIELD OF THE INVENTION

The present invention relates to a novel sustained release drug delivery device comprising an inner core or reservoir containing an agent effective in obtaining a desired local or systemic physiological or pharmacological effect; a first coating which is permeable to the passage of the effective agent; a second coating containing an impermeable polymer and at least one impermeable disc essentially impermeable to the passage of the effective agent; and a third coating permeable to the passage of the effective agent. The first coating covers at least a portion of the inner core. The second coating covers at least a portion of the first coating layer and inner core; however, at least a small portion of the first coating layer or inner core is not coated with the second coating layer. The third coating layer essentially completely covers the first coating layer and the second coating layer. The portion of the first coating layer which is not coated with the second coating layer allows passage of the agent into the third coating layer thus allowing controlled release.

BACKGROUND OF THE INVENTION

Over the years, various drugs have been developed to assist in the treatment of a wide variety of ailments and diseases. However, in many instances such drugs are not capable of being administered either orally or intravenously without the risk of various detrimental side effects.

For example, intravenous ganciclovir (GCV) is effective in the treatment of CMV retinitis in AIDS patients, but bone marrow toxicity limits its usefulness. The incidence of neutropenia (absolute neutrophil count < 1000) during intravenous GCV therapy ranges from 30 to 50%. Continuous maintenance GCV therapy is necessary to prevent progression or recrudescence of the disease, but despite maintenance therapy 30 to 50% of patients experience a relapse during treatment. Other problems associated with systemic GCV administration include the risk of sepsis related to permanent indwelling catheters and the inability to receive concurrent therapy with zidovudine (AZT) which has been shown to prolong life and improve the immune function in AIDS patients.

Intravitreal GCV injections of 200 to 400 $\mu$g administered once or twice weekly have resulted in temporary remission of CMV retinitis in AIDS patients. Intravitreal GCV injections may provide a higher intraocular drug concentration than systemic therapy and reduce the incidence of neutropenia. Current treatment of CMV retinitis in AIDS patients is clearly suboptimal. Ganciclovir is virustatic and thus disease inhibition requires maintenance drug administration.

Due to the risks that certain drugs impose, researchers have developed systems for administering such drugs to aid in the treatment of these ailments and diseases. Many of these systems provide a release rate which reduces the occurrence of detrimental side effects.

One such delivery device is an orally administered pill or capsule which contains a drug encapsulated within various layers of a composition that dissolves over a period of time in the digestive tract, thereby allowing a gradual or slow release of the drug into the system.

Another type of device for controlling the administration of such drugs is produced by coating a drug with a polymeric material permeable to the passage of the drug to obtain the desired effect. Such devices are particularly suitable for treating a patient at a specific local area without having to expose the patient's entire body to the drug. This is advantageous because many possible side effects of the drug could be minimized.

Such systems are particularly suitable for treating ailments affecting the eye. Advances for administering a drug to the external surface of the eye are disclosed in U.S. Pat. No. 4,014,335 to Arnold. Arnold describes various ocular inserts that act as a deposit or drug reservoir for slowly releasing a drug into the tear film for prolonged periods of time. These inserts are fabricated of a flexible polymeric material that is biologically inert, non-allergenic, and insoluble in tear fluid. To initiate the therapeutic programs of these devices, the ocular inserts are placed in the cul-de-sac between the sclera of the eyeball and the eyelid for administering the drug to the eye.

Devices formed of polymeric materials that are insoluble in tear fluid retain their shape and integrity during the course of the needed therapy to serve as a drug reservoir for continuously administering a drug to the eye and the surrounding tissues at a rate that is not effected by dissolution or erosion of the polymeric material. Upon termination of the desired therapeutic program, the device is removed from the cul-de-sac.

Another type of device used for sustained release of a drug to the external surface of the eye, described in U.S. Pat. No. 3,416,530, is manufactured with a plurality of capillary openings that communicate between the exterior of the device and the interior chamber generally defined from a polymeric membrane. While these capillary openings in this construction are effective for releasing certain drugs to the eye, they add considerable complexity to the manufacture of the device because it is difficult to control the size of these openings in large scale manufacturing using various polymers.

Another device, described in U.S. Pat. No. 3,618,604, does not involve such capillary openings, but instead provides for the release of the drug by diffusion through a polymeric membrane. The device, in a preferred embodiment, as disclosed in that patent, comprises a sealed container having the drug in an interior chamber. Nonetheless, as described in U.S. Pat. No. 4,014,335, certain problems have been identified with such devices such as the difficult task of sealing the margins of the membrane to form the container. In addition, stresses and strains introduced into the membrane walls from deformation during manufacturing of those devices may cause the reservoir to rupture and leak.

Another such device, described in U.S. Pat. No. 4,014,335, comprises a three-layered laminant having a pair of separate and discrete first and third walls formed of a material insoluble in tear fluid with one of the walls formed of a drug release material permeable to the passage of drug and the other wall formed of a material impermeable to the passage of the drug.

The above described systems and devices are intended to provide sustained release of drugs effective in treating patients at a desired local or systemic level for obtaining certain physiological or pharmacological effects. However, there are many disadvantages associated with their use including the fact that it is often times difficult to obtain the desired release rate of the drug. The need for a better release system is especially significant in the treatment of CMV retinitis.

Prior to the development of the present invention, there was developed a novel sustained release delivery device which ameliorated many of the aforementioned problems associated with drug delivery. The device, which is disclosed in U.S. Pat. No. 5,378,475, included a first coating essentially impermeable to the passage of the effective agent and a second coating permeable to the passage of the effective agent. In the device, the first coating covered at least a portion of the inner core; however, at least a small portion of the inner core is not coated with the first coating layer. The second coating layer essentially completely covers the first coating layer and the uncoated portion of the inner core. The portion of the inner core which is not coated with the second coating layer allows passage of the agent into the second coating layer thus allowing controlled release.

While the devices described in U.S. Pat. No. 5,378,475 solve many of the aforementioned problems pertaining to drug delivery, the devices and the method of making the devices are not without problems. In particular, polymers suitable for coating the inner core are frequently relatively soft and technical difficulties can arise in production of uniform films. This is especially true when attempting to coat non-spherical bodies with edges (such as a cylindrical shape). In such case, relatively thick films must be applied to achieve uninterrupted coatings. Thus, the devices tend to be larger than necessary as a result of the thickness needed to seal the ends of the inner core.

The problem of device size is extremely important in the design of devices for implantation into limited anatomical spaces such as the eye. Larger devices require more complex surgery to both implant and remove. Furthermore, the extra polymer required to achieve a uniform coating reduces the potential volume of the implant and hence limits the amount of drug that can be delivered.

As a result of all of the above, there remains a need in the art for improving the design and the method of preparing devices which provide a sustained release of a drug to a patient to obtain a desired local or systemic physiological or pharmacological effect especially for ocular use.

SUMMARY OF THE INVENTION

It is, therefore, a primary objective of the present invention to provide a device suitable for the controlled and sustained release of a composition effective in obtaining a desired local or systemic physiological or pharmacological effect.

The device, in one embodiment, includes an inner core or reservoir which contains an agent effective in obtaining the desired effect. The device further includes a first coating layer. The first coating layer is permeable to the passage of the agent. In addition, the device includes a second coating layer which includes at least one impermeable disc and an impermeable polymer. The second coating layer is essentially impermeable to the passage of the agent and covers a portion of the first coating layer and inner core. The second coating layer blocks passage of the agent from the inner core at those sides where it contacts the first coating layer. The remaining portion of the inner core which is not blocked allows a controlled amount of the agent from the inner core to pass into the first coating layer via a passage in the second coating layer, into a third coating layer. The third coating layer is permeable to the passage of the agent and covers essentially the entire second coating layer. The second coating layer is positioned between the inner core and the third coating layer in order to control the rate at which the agent permeates through the third coating layer.

Another object of the present invention is to provide a method for treating a mammalian organism, e.g., human, to obtain a desired local or systemic physiological or pharmacological effect. The method includes positioning the sustained released drug delivery system at an area wherein release of the agent is desired and allowing the agent to pass through the third coating to the desired area of treatment.

Another object of the present invention is to provide an ocular device suitable for direct implantation into the vitreous of the eye. Such devices of the present invention are surprisingly found to provide sustained controlled release of various compositions to treat the eye without risk of detrimental side effects.

Another object of the present invention is to maximize the amount of drug contained in an intraocular device while minimizing its size in order to prolong the duration of the implant.

Another object of the present invention is to provide an ocular delivery system that could be applied to an intraocular lens to prevent inflammation or posterior capsular opacification.

With the foregoing as well as other objects, advantages, features and aspects of the invention that will become hereinafter apparent, the nature of the invention may be more clearly understood by reference to the detailed description of the invention and to the appended claims.

DETAILED DESCRIPTION OF THE PREFERRED EMBODIMENTS OF THE INVENTION

More specifically, the present inventors have discovered a device and method of preparation thereof that is suitable for the controlled and sustained release of an agent effective in obtaining a desired local or systemic physiological or pharmacological effect. In particular, it has been found that by sealing at least one surface with an impermeable disc, thinner coatings may be utilized. This has the advantage of enabling thinner, shorter devices to be prepared than otherwise possible. A further advantage is that as the material used to prepare the impermeable disc need not be malleable (to facilitate covering of a curved surface); instead relatively hard materials can be used to ease creation of uniform diffusion ports.

The device includes an inner core or reservoir which contains an agent effective in obtaining a desired effect. The device further includes a first coating layer, a second coating layer and a third coating layer. The first coating layer which is permeable to the passage of the effective agent may completely cover the inner core. The second coating layer covers only a portion of the first coating layer and inner core and is impermeable to the passage of the agent. The third coating layer covers all of the first coating layer and second coating layer and is permeable to the passage of the agent. The portion of the first coating layer and inner core that is not coated with the second coating layer facilitates passage of the agent through the third coating layer. Specifically, the second coating layer is positioned between the inner core and the third coating layer such that it blocks the passage of the agent through the adjacent portions of the third coating layer thus controlling the rate of passage of the agent.

Figure 1:
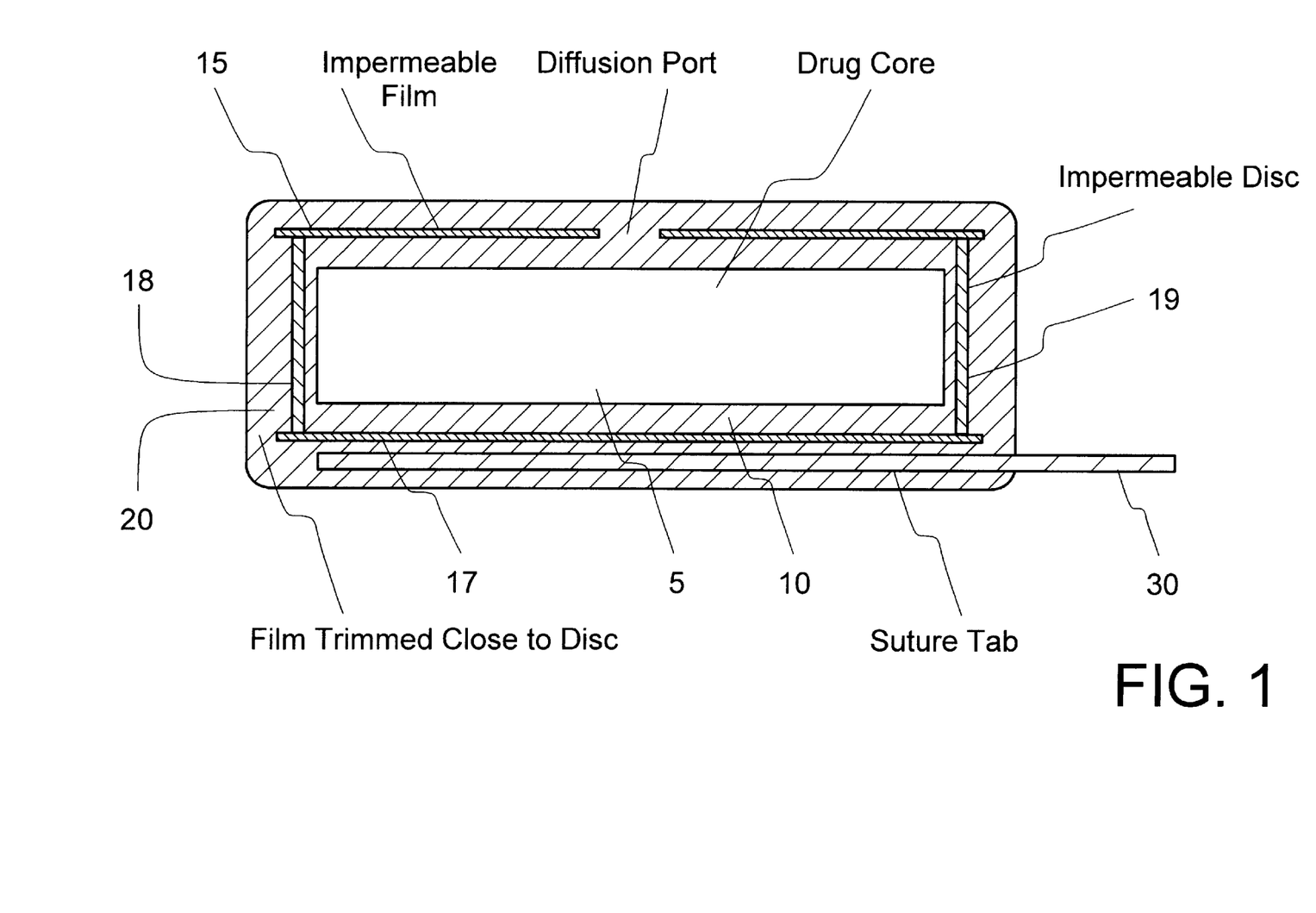
FIG. 1 is an enlarged view of one embodiment of the sustained release drug delivery device showing inner core, first coating layer, second coating layer and third coating layer.

FIG. 1 illustrates one embodiment of the sustained release drug delivery device of the present invention. While the device shown in FIG. 1 is cylindrical, the device could be any shape. The device comprises an inner core or reservoir 5, a permeable coating 10 which is permeable to the passage of the agent in the core or reservoir, an impermeable coating 15 which is impermeable to the passage of the agent in the core or reservoir 5, and a permeable coating 20 which is permeable to the passage of the agent in the core or reservoir 5. The second coating includes an impermeable polymer 17 and discs 18 and 19 at the ends of the cylindrical core. FIG. 1 further shows a suture tag 30.

Figure 2A:
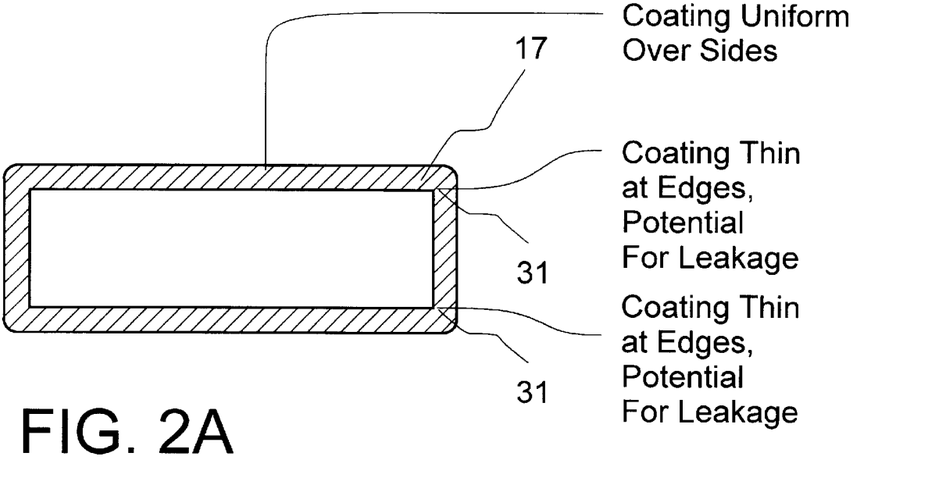
FIG. 2A is an enlarged view of the impermeable polymer.
Figure 2B:
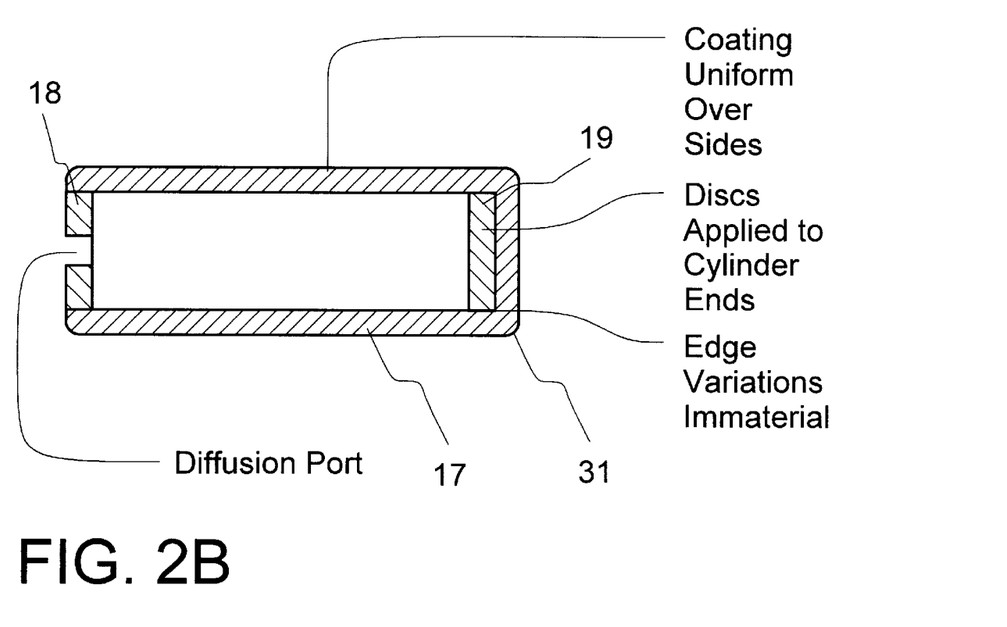
FIG. 2B is an enlarged view of the second coating layer including the impermeable film and impermeable disc.

FIGS. 2A and 2B show only the second coating layer and illustrate the benefits associated with using impermeable discs as a portion of the second layer. FIG. 2A shows the impermeable polymeric layer 17 thinly coating the edges of the inner core. The thinly coated edges 31 create a potential for leakage of the effective agent.

FIG. 2B illustrates the benefits of using impermeable discs. The second coating layer contains the impermeable polymer 17 and the impermeable discs 18 and 19 at the ends of the cylindrical core. The impermeable disc 18 contains a diffusion port. The impermeable discs 18 and 19 prevent the leakage of the effective agent through the thin edges 31 of the impermeable polymer.

The invention further relates to a method for treating a mammalian organism to obtain a desire local or systemic physiological or pharmacological effect. The method includes administering the sustained release drug delivery system to the mammalian organism and allowing the agent effective in obtaining the desired local or systemic effect to pass through the third coating to contact the mammalian organism. The term administering, as used herein, means positioning, inserting, injecting, implanting, or any other means for exposing the device to a mammalian organism. The route of administration depends on a variety of factors including type of response or treatment, type of agent and preferred site of administration.

The devices in certain embodiments have applicability in providing a controlled and sustained release of agents effective in obtaining a desired local or systemic physiological or pharmacological effect relating at least to the following areas: treatment of cancerous primary tumors, (e.g., glioblastoma); chronic pain; arthritis; rheumatic conditions; hormonal deficiencies such as diabetes and dwarfism; and modification of the immune response such as in the prevention of transplant rejection and in cancer therapy. A wide variety of other disease states may also be prevented or treated using the drug delivery device of the present invention. Such disease states are known by those of ordinary skill in the art. For those not skilled in the art, reference may be made to Goodman and Gilman, *The Pharmacological Basis of Therapeutics*, 8th Ed., Pergamon Press, New York, 1990; and *Remington's Pharmaceutical Sciences*, 18th Ed., Mack Publishing Co., Easton, Pa., 1990; both of which are incorporated by reference herein.

In addition, the devices are suitable for use in treating mammalian organisms infected with AIDS and AIDS related opportunistic infections such as cytomegalovirus infections, toxoplasmosis, pneumocystis carinii and mycobacterium avium intercellular.

The devices are particularly suitable for treating ocular conditions such as glaucoma, proliferative vitreoretinopathy, diabetic retinopathy, uveitis, and keratitis. The devices are also particularly suitable for use as an ocular device in treating mammalian organisms suffering from cytomegalovirus retinitis wherein the device is surgically implanted within the vitreous of the eye.

As described above, the inner core or reservoir contains an agent effective in obtaining a desired local or systemic physiological or pharmacological effect. The following classes of agents could be incorporated into the devices of the present invention: anesthetics and pain killing agents such as lidocaine and related compounds and benzodiazepam and related compounds; anti-cancer agents such as 5-fluorouracil, adriamycin and related compounds; antiinflammatory agents such as 6-mannose phosphate; anti-fungal agents such as fluconazole and related compounds; anti-viral agents such as trisodium phosphomonoformate, trifluorothymidine, acyclovir, ganciclovir, DDI and AZT; cell transport/mobility impending agents such as colchicine, vincristine, cytochalasin B and related compounds; antiglaucoma drugs such as beta-blockers: timolol, betaxolol, atenalol, etc; immunological response modifiers such as muramyl dipeptide and related compounds; peptides and proteins such as cyclosporin, insulin, growth hormones, insulin related growth factor, heat shock proteins and related compounds; steroidal compounds such as dexamethasone, prednisolone and related compounds; low solubility steroids such as fluocinolone acetonide and related compounds; and carbonic anhydrize inhibitors.

In addition to the above agents, other agents are suitable for administration to the eye and its surrounding tissues to produce a local or a systemic physiologic or pharmacologic beneficial effect. Examples of such agents include neuroprotectants such as nimodipine and related compounds; antibiotics such as tetracycline, chlortetracycline, bacitracin, neomycin, polymyxin, gramicidin, oxytetracycline, chloramphenicol, gentamycin, and erythromycin; antibacterials such as sulfonamides, sulfacetamide, sulfamethizole and sulfisoxazole; antivirals, including idoxuridine; and other antibacterial agents such as nitrofurazone and sodium propionate; antiallergenics such as antazoline, methapyriline, chlorpheniramine, pyrilamine and prophenpyridamine; anti-inflammatories such as hydrocortisone, hydrocortisone acetate, dexamethasone 21-phosphate, fluocinolone, medrysone, methylprednisolone, prednisolone 21-phosphate, prednisolone acetate, fluoromethalone, betamethasone and triminolone; decongestants such as phenylephrine, naphazoline, and tetrahydrazoline; miotics and anti-cholinesterase such as pilocarpine, eserine salicylate, carbachol, di-isopropyl fluorophosphate, phospholine iodine, and demecarium bromide; mydriatics such as atropine sulfate, cyclopentolate, homatropine, scopolamine, tropicamide, eucatropine, and hydroxyamphetamine; sympathomimetics such as epinephrine; and prodrugs such as those described in *Design of Prodrugs,* edited by Hans Bundgaard, Elsevier Scientific Publishing Co., Amsterdam, 1985. Once again, reference may be made to any standard pharmaceutical textbook such as *Remington's Pharmaceutical Sciences* for the identify of other agents.

Any pharmaceutically acceptable form of such a compound may be employed in the practice of the present invention, i.e., the free base or a pharmaceutically acceptable salt or ester thereof. Pharmaceutically acceptable salts, for instance, include sulfate, lactate, acetate, stearate, hydrochloride, tartrate, maleate and the like.

A large number of polymers can be used to construct the devices of the present invention. The only requirements are that they are inert, non-immunogenic and of the desired permeability.

Materials that may be suitable for fabricating the device include naturally occurring or synthetic materials that are biologically compatible with body fluids and eye tissues, and essentially insoluble in body fluids with which the material will come in contact. The use of rapidly dissolving materials or materials highly soluble in eye fluids are to be avoided since dissolution of the wall would affect the constancy of the drug release, as well as the capability of the system to remain in place for a prolonged period of time.

Naturally occurring or synthetic materials that are biologically compatible with body fluids and eye tissues and essentially insoluble in body fluids which the material will come in contact include, but are not limited to, polyvinyl acetate, cross-linked polyvinyl alcohol, cross-linked polyvinyl butyrate, ethylene ethylacrylate copolymer, polyethyl hexylacrylate, polyvinyl chloride, polyvinyl acetals, plasiticized ethylene vinylacetate copolymer, polyvinyl alcohol, polyvinyl acetate, ethylene vinylchloride copolymer, polyvinyl esters, polyvinylbutyrate, polyvinylformal, polyamides, polymethylmethacrylate, polybutylmethacrylate, plasticized polyvinyl chloride, plasticized nylon, plasticized soft nylon, plasticized polyethylene terephthalate, natural rubber, polyisoprene, polyisobutylene, polybutadiene, polyethylene, polytetrafluoroethylene, polyvinylidene chloride, polyacrylonitrile, cross-linked polyvinylpyrrolidone, polytrifluorochloroethylene, chlorinated polyethylene, poly (1,4'-isopropylidene diphenylene carbonate), vinylidene chloride, acrylonitrile copolymer, vinyl chloride-diethyl fumerale copolymer, silicone rubbers, especially the medical grade polydimethylsiloxanes, ethylene-propylene rubber, silicone-carbonate copolymers, vinylidene chloride-vinyl chloride copolymer, vinyl chloride-acrylonitrile copolymer and vinylidene chloride-acrylonitride copolymer.

Specifically, the second layer of the device of the present invention may be made of any of the above-listed polymers or any other polymer which is biologically compatible with body fluids and eye tissues, essentially insoluble in body fluids which the material will come in contact and essentially impermeable to the passage of the effective agent. The term impermeable, as used herein, means that the layer will not allow passage of the effective agent at a rate required to obtain the desired local or systemic physiological or pharmacological effect.

The second layer must be selected to be impermeable, as described above, to the passage of the agent from the inner core out to adjacent portions of the second coating layer. The purpose is to block the passage of the agent to those portions and thus control the release of the agent out of the drug delivery device.

The composition of the second layer, e.g., the polymer, must be selected so as to allow the above-described controlled release. The preferred composition of the second layer will vary depending on such factors as the active agent, the desired rate of control and the mode of administration. The identity of the active agent is important since the size of the molecule, for instance, is critical in determining the rate of release of the agent into the second layer.

The disc is essentially impermeable to the passage of the effective agent and may cover a portion of the inner core not covered by the impermeable film of the second coating layer. As shown in FIG. 2B, the disc may cover edges of the inner core and enables a thinner uniform coat of the impermeable film to be applied over the inner core than would otherwise be possible. In one embodiment, the impermeable film may completely cover the inner core and the discs. Drug release may occur via passage through a hole in the disc (see FIG. 2B) or a hole in the impermeable film. The physical properties of the polymer used for the disc can be selected based on their ability to withstand subsequent processing steps (such as heat curing) without suffering deformation of the hole. The polymer for the impermeable film can be selected based on the ease of coating the inner core. Possible materials for the disc include, Teflon, polycarbonate, polymethyl methacrylate, polyethylene alcohol, high grades of ethylene vinyl acetate (9% vinyl, content) and polyvinyl alcohol.

Since the second coating layer is essentially impermeable to the passage of the effective agent, only a portion of the inner core or reservoir and first coating layer may be coated with the second coating layer. Depending on the desired delivery rate of the device, the second coating layer may coat only a small portion of the surface area of the inner core for faster release rates of the effective agent or may coat large portions of the surface area of the inner core for slower release rates of the effective agent.

At least 50% of the surface area may be coated by the second coating layer. For slower release rates, at least 75% of the surface area may be coated. For even slower release rates, at least 95% of the surface area may be coated.

Thus, any portion of the surface area of the first coating layer and inner core up to but not including 100% may be coated with the second coating layer as long as the desired rate of release of the agent is obtained.

The second coating, including the impermeable film and impermeable disc, may be positioned anywhere over the inner core and first coating layer, including but not limited to the top, bottom or any side of the first coating layer and inner core. In addition, it could be on the top and a side, or the bottom and a side, or the top and the bottom, or on opposite sides or on any combination of the top, bottom or sides.

The first and third layer of the device of the present invention must be biologically compatible with body fluids and eye tissues, essentially insoluble in body fluids which the material will come in contact and permeable to the passage of the agent or composition effective in obtaining the desired effect.

The effective agent diffuses in the direction of lower chemical potential, i.e., toward the exterior surface of the device. At the exterior surface of the device, equilibrium is again established. When the conditions on both sides of the third coating layer are maintained constant, a steady state flux of the effective agent will be established in accordance with Fick's Law of Diffusion. The rate of passage of the drug through the material by diffusion is generally dependent on the solubility of the drug therein, as well as on the thickness of the wall. This means that selection of appropriate materials for fabricating the wall will be dependent on the particular drug to be used.

The rate of diffusion of the effective agent through a polymeric layer of the present invention may be determined via diffusion cell studies carried out under sink conditions. In diffusion cell studies carried out under sink conditions, the concentration of drug in the receptor compartment is essentially zero when compared to the high concentration in the donor compartment. Under these conditions, the rate of drug release is given by:

$$Q/t = (D \cdot K \cdot A \cdot DC)/h$$

where Q is the amount of drug released, t is time, D is the diffusion coefficient, K is the partition coefficient, A is the surface area, DC is the difference in concentration of the drug across the membrane, and h is the thickness of the membrane.

In the case where the agent diffuses through the layer via water filled pores, there is no partitioning phenomena. Thus, K can be eliminated from the equation. Under sink conditions, if release from the donor side is very slow, the value DC is essentially constant and equal to the concentration of the donor compartment. Release rate therefore becomes dependent on the surface area (A), thickness (h) and diffusivity (D) of the membrane. In the construction of the device of the present invention, the size (and therefore, surface area) is mainly dependent on the size of the effective agent.

Thus, permeability values may be obtained from the slopes of a Q versus time plot. The permeability P, can be related to the diffusion coefficient D, by:

$$P=(K \cdot D)/h$$

Once the permeability is established for the coating permeable to the passage of the agent, the surface area of the agent that must be coated with the coating impermeable to the passage of the agent may be determined. This is done by progressively reducing the available surface area until the desired release rate is obtained.

Exemplary microporous materials suitable for use as a first and third coating layer, for instance, are described in U.S. Pat. No. 4,014,335 which is incorporated herein by reference in its entirety. These materials include cross-linked polyvinyl alcohol, polyolefins or polyvinyl chlorides or cross-linked gelatins; regenerated, insoluble, nonerodible cellulose, acylated cellulose, esterified celluloses, cellulose acetate propionate, cellulose acetate butyrate, cellulose acetate phthalate, cellulose acetate diethyl-aminoacetate; polyurethanes, polycarbonates, and microporous polymers formed by co-precipitation of a polycation and a polyanion modified insoluble collagen. Cross-linked polyvinyl alcohol is preferred. The third coating layer is selected so as to slow release of the agent from the inner core into contact with a mammalian organism, e.g., a human. The third coating layer need not provide gradual release or control of the agent into the biological environment, however, the third coating layer may be advantageously selected to also have that property or feature.

The devices of the present invention may be made in a wide variety of ways, such as by obtaining an effective amount of the agent and compressing the agent to a desired shape. Once shaped, the first coating layer may be applied. The first coating layer may be applied by dipping the device one or more times in a solution containing the desired polymer. Optionally, the first coating may be applied by dropping, spraying, brushing or other means of coating the outer surface of the device with the polymer solution. When using a polyvinyl alcohol solution to obtain the second coating layer, the desired thickness may be obtained by applying several coats. Each coat may be dried prior to applying the next coat. Finally, the device may be heated to adjust the permeability of the outer coating.

The impermeable disc may be applied directly over the first layer before coating with the impermeable polymer layer. In the case of a cylindrical core, an impermeable film may be wrapped around the core after discs are applied to one or both ends. Thus, the second coating layer includes both the impermeable film and the impermeable discs. By sealing at least one surface with an impermeable disc, thinner layers may be utilized. This has the advantage of enabling thinner, shorter devices to be prepared than otherwise possible.

The impermeable polymer layer should be thick enough to prevent release of drug across it except for the area not covered (the diffusion layer or port). Due to the desirability of minimizing the size of the implants, the thickness of the impermeable film layer therefore can be 0.01 to 2 millimeters, preferably 0.01 to less than 0.5 millimeters.

The impermeable disc should also be thick enough to prevent drug release across it save though a specifically prepared membrane or port. Due to the desirability of minimizing the size of the implants, the thickness of the impermeable disc can be 0.01 to 2 millimeters, preferably 0.01 to less than 1 millimeter.

Once the second coating layer, including the impermeable disc(s), is applied to the device, the third coating layer may be applied. The third coating may be applied by dipping the device one or more times in a solution containing the desired polymer. Optionally, the third coating layer may be applied by dropping, spraying, brushing or other means of coating the outer surface of the device with the polymer solution. When using a polyvinyl alcohol solution to obtain the third coating layer, the desired thickness may be obtained by applying several coats. Each coat may be dried prior to applying the next coat. Finally, the device may be heated to adjust the permeability of the outer coating.

The above description of how to make the devices of the present invention is merely illustrative and should not be considered as limiting the scope of the invention in any way, as various compositions are well known by those skilled in the art. In particular, the methods of making the device depends on the identity of the active agent and polymers selected. Given the active agent, the composition of the first coating, the second coating (the film and disc), and the third coating, one skilled in the art could easily make the devices of the present invention using conventional coating techniques.

The method for treating a mammalian organism to obtain a desired local or systemic physiological or pharmacological effect includes administering the sustained release drug delivery device of the present invention to the mammalian organism and allowing the agent to pass through the device to come in direct contact with the mammalian organism.

The drug delivery system of the present invention may be administered to a mammalian organism via any route of administration known in the art. Such routes of administration include intraocular, oral, subcutaneous, intramuscular, intraperitoneal, intranasal, dermal, and the like. In addition, one or more of the devices may be administered at one time or more than one agent may be included in the inner core.

The drug delivery system of the present invention is particularly suitable for direct implantation into the vitreous of the eye and for application to an intraocular lens.

These methods of administration and technique for their preparation are well known by those of ordinary skill in the art. Techniques for their preparation are set forth in *Remington's Pharmaceutical Sciences.*

The drug delivery system may be administered for a sufficient period of time and under conditions to allow treatment of the disease state of concern.

For localized drug delivery, the devices may be surgically implanted at or near the site of action. This is the case for devices of the present invention used in treating ocular conditions, primary tumors, rheumatic and arthritic conditions, and chronic pain.

For systemic relief, the devices may be implanted subcutaneously, intramuscularly or intraperitoneally. This is the case when devices are to give sustained systemic levels and avoid premature metabolism. In addition, such devices may be administered orally.

In one embodiment of the invention, an ocular device containing ganciclovir as the effective agent in an effective amount to prevent a virus from replicating may be prepared. Such devices may be used to effectively combat and inhibit reproduction of cytomegalovirus retinitis, when surgically implanted into the vitreous of the eye. Such devices may remain in the vitreous permanently after treatment is complete. The preferred amount of ganciclovir used in these devices ranges from about 0.01 mg to about 40 mg. More preferably, such devices contain from about 15 mg to about 30 mg of ganciclovir. These preferred ranges may provide sustained release of the ganciclovir for a period of from several hours to over two years. The preferred first coating is polyvinyl alcohol. The preferred impermeable disc is Teflon or ethyl vinyl alcohol. The preferred impermeable polymer is ethylene vinyl acetate. The preferred third coating layer is polyvinyl alcohol. When such devices are prepared for implantation within the vitreous of the eye, it is preferred that the device does not exceed about 7 millimeters in any direction. Thus, the cylindrical device shown in FIG. 1 would preferably not exceed 7 millimeters in height or 3 millimeters in diameter. The preferred thickness of the first coating layer ranges from about 0.05 to about 0.5 millimeters. The preferred thickness of the second coating layer ranges from about 0.1 to about 1.0 millimeters. The preferred thickness of the third coating layer ranges from about 0.1 to about 2.0 millimeters.

In another embodiment of the invention, an ocular device containing nimodipine as the effective agent may be prepared. As further shown in the examples which follow, such devices may be used to provide long term sustained release of nimodipine for several years. The preferred amount of nimodipine used in these devices ranges from 2 to 15 mg. More preferable, such devices contain approximately 10–15 mg. These preferred ranges may provide sustained release of the nimodipine for a period in excess of 10 years. The preferred materials include polyvinyl alcohol as the first layer, one end of the cylindrical device covered by a disc of ethylene vinyl acetate (9%) and the other uncovered, ethylene vinyl acetate (19%) as the impermeable polymer layer covering the sides of the cylinder and the end sealed with the disc, and a third layer, silicone, covering the entire assembly. The preferred thickness of the first layer ranges from 0.05 to 0.2 millimeters. The preferred thickness of the impermeable polymer layer ranges from 0.05 to 0.15 millimeters, preferably 0.75 millimeters. The preferred thickness for the disc ranges from 0.05 to 2 millimeters and the preferred thickness of the third layer ranges from 0.1 to 0.5 millimeters.

In another embodiment of the invention, an ocular device containing fluocinolone acetonide as the effective agent may be prepared. As further shown in the Examples which follow, such devices may be used to provide sustained release of fluocinolone acetonide for several years. The preferred amount of fluocinolone acetonide used in these devices ranges from 2 to 15 mg. More preferably, such devices contain approximately 5 to 10 mg. These preferred ranges may provide sustained release of the fluocinolone acetonide for a period of 3 years. The overall diameter of the device is 2 millimeters and the length is 5 millimeters.

The preferred materials include polyvinyl alcohol as the first layer, one end of the cylindrical device covered by a disc of ethylene vinyl acetate (9%) and the other uncovered, ethylene vinyl acetate (19%) as the impermeable polymer layer covering the sides of the cylinder, and the end sealed with the disc, and a third layer, polyvinyl alcohol, covering the entire assembly. The preferred thickness of the first layer ranges from 0.05 to 0.2 millimeters. The thickness of the impermeable polymer layer may range from 0.05 to 0.15 millimeters and is preferably 0.75 millimeters. The preferred thickness for the disc ranges from 0.05 to 2 millimeters and the preferred thickness of the third layer ranges from 0.1 to 0.5 millimeters.

While the above described embodiments of the invention are described in terms of preferred ranges of the amount of effective agent, and preferred thicknesses of the preferred first and second coating, these preferences are by no means meant to limit the invention. As would be readily understood by one skilled in the art, the preferred amounts, materials and dimensions depend on the method of administration, the effective agent used, the polymers used, the desired release rate and the like. Likewise, actual release rates and release duration depend on a variety of factors in addition to the above, such as the disease state being treated, the age and condition of the patient, the route of administration, as well as other factors which would be readily apparent to those skilled in the art.

From the foregoing description, one of ordinary skill in the art can easily ascertain the essential characteristics of the instant invention, and without departing from the spirit and scope thereof, can make various changes and/or modifications of the invention to adapt it to various usages and conditions. As such, these changes and/or modifications are properly, equitably and intended to be, within the full range of equivalence of the following claims.

What is claimed is:

1. A method for treating a mammalian organism to obtain a desired local or systemic physiological or pharmacological effect comprising:

administering a sustained release drug delivery system to a mammalian organism in need of such treatment, said drug delivery system comprising;
  (1) an inner core or reservoir comprising an effective amount of an agent to obtain a desired local or systemic physiological or pharmacological effect,
  (2) a first coating layer permeable to the passage of said agent, wherein said first coating layer covers at least a portion of said inner core, which provides control and sustained release of the agent,
  (3) a second coating layer, said second coating layer essentially impermeable to the passage of said agent, and said second coating layer covering at least 50% of the inner core and/or the first coating layer, wherein at least a small portion of the inner core or first coating layer is not coated with said second coating layer and said second coating layer comprises an impermeable film and at least one impermeable disc being different material from or having substantially greater hardness, thickness, malleability or response to heat curing than said impermeable film, and
  (4) a third coating layer permeable to the passage of said agent, wherein said third coating layer essentially completely covers said second coating layer and the uncoated portion of the first coating layer or inner core, whereby said agent is able to pass through said third coating layer in a controlled manner.

2. A method for treating a mammalian organism as claimed in claim 1, wherein said third coating layer comprises polyvinyl alcohol.

3. A method for treating a mammalian organism as claimed in claim 2, wherein said second coating layer comprises ethylene vinyl acetate.

4. A method for treating a mammalian organism as claimed in claim 3, wherein said first coating layer comprises polyvinyl alcohol.

5. A method for treating a mammalian organism as claimed in claim 1, wherein said effective agent comprises fluocinolone acetonide, nimodipine or ganciclovir.

6. A method for treating a mammalian organism for cytomegalovirus retinitis comprising:

administering a sustained release drug delivery system to a mammalian organism in need of such treatment, said drug delivery system comprising;
  (1) an inner core or reservoir comprising an effective amount of ganciclovir effective to obtain a desired local or systemic physiological or pharmacological effect,
  (2) a first coating layer permeable to the passage of said agent, said first coating layer essentially completely covers said inner core,
  (3) a second coating layer, said second coating layer essentially impermeable to the passage of said ganciclovir, and said second coating layer covering at least 50% of the inner core and/or the first coating layer, wherein at least a small portion of the inner core or first coating layer is not coated with said second coating layer, and wherein said second coating layer comprises an impermeable film and at least one impermeable disc being a different material from or having substantially greater hardness, thickness, malleability or response to heat curing than said impermeable film, and (4) a third coating layer permeable to the passage of said ganciclovir, wherein said third coating layer essentially completely covers said second coating layer and the uncoated portion of the first coating layer or inner core, whereby said ganciclovir is able to pass through said third coating layer in a controlled manner.

7. A method for providing controlled and sustained administration of an agent effective in obtaining a desired local or systemic physiological or pharmacological effect comprising:
surgically implanting a sustained release drug delivery system at a desired location, said drug delivery system comprising;
(1) an inner core or reservoir comprising an effective amount of an agent effective in obtaining a desired physiological or pharmacological effect, and
(2) a first coating layer permeable to the passage of said agent, wherein said first coating layer covers at least a portion of said inner core, which provides control and sustained release of the agent,
(3) a second coating layer, said second coating layer essentially impermeable to the passage of said agent, and said second coating layer covering at least 50% of the inner core and/or the first coating layer, wherein at least a small portion of the inner core or first coating layer is not coated with said second coating layer and said second coating layer comprises an impermeable film and at least one impermeable disc being a different material from or having substantially greater hardness, thickness, malleability or response to heat curing than said impermeable film, and
(4) a third coating layer permeable to the passage of said agent, wherein said third coating layer essentially completely covers said second coating layer and the uncoated portion of the first coating layer or inner core, whereby said agent is able to pass through said third coating layer in a controlled manner.

8. A method as claimed in claim 7, wherein said device is surgically implanted within the vitreous of the eye.

9. A method as claimed in claim 7, wherein said first and third coating layers comprise polyvinyl alcohol.

10. A method as claimed in claim 7 wherein said third coating layer is silicone.

11. A method as claimed in claim 9, wherein said second coating layer comprises ethylene vinyl acetate.

12. A method as claimed in claim 11, wherein said effective agent is ganciclovir or 5-fluorouracil.

13. A method as claimed in claim 11 wherein said effective agent is a low solubility steroid.

14. A method as claimed in claim 13, wherein said low solubility steroid is fluocinolone acetonide.

15. A method as claimed in claim 11 wherein said effective agent is a neuroprotectant.

16. A method as claimed in claim 15, wherein said neuroprotectant is nimodipine.

17. A sustained release drug delivery system comprising:
(A) an inner core or reservoir comprising an effective amount of an agent effective in obtaining a desired local or systemic physiological or pharmacological effect,
(B) a first coating layer permeable to the passage of said agent, wherein said first coating layer covers at least a portion of said inner core, which provides control and sustained release of the agent,
(C) a second coating layer, said second coating layer impermeable to the passage of said effective agent, and said second coating layer covering at least 50% of the inner core and/or the first coating layer wherein at least a small portion of the inner core or first coating layer is not coated with said second coating layer and said second coating layer comprises an impermeable film and at least one impermeable disc being a different material from or having substantially greater hardness, thickness, malleability or response to heat curing than said impermeable film, and
(D) a third coating layer, said third coating layer permeable to the passage of said effective agent, wherein said third coating layer essentially completely covers the second coating layer and the uncoated portion of the first coating layer or inner core.

18. A sustained release drug delivery system as claimed in claim 17, wherein said third coating layer comprises polyvinyl alcohol.

19. A sustained release drug delivery system as claimed in claim 18, wherein said second coating layer comprises ethylene vinyl acetate.

20. A sustained release drug delivery system as claimed in claim 19, wherein said first coating layer comprises polyvinyl alcohol.

21. A sustained release drug delivery system as claimed in claim 20, wherein said effective agent is ganciclovir or fluocinolone acetonide.

22. A sustained release drug delivery system as claimed in claim 17, wherein said effective agent is nimodipine.

23. A sustained release drug delivery system as claimed in claim 17, wherein the third coating layer comprises silicone.

24. A method for treating a mammalian organism according to claim 1, wherein said impermeable film is made of a composition different from said impermeable disc.

25. A method for treating a mammalian organism as claimed in claim 1, wherein said second coating layer covers all of the inner core and first coating layer except for a diffusion port opening.

26. A method for treating a mammalian organism as claimed in claim 1, wherein said impermeable disc is harder than said impermeable film.

27. The sustained release drug delivery system as claimed in claim 17, wherein said effective agent is a steroid.

28. The sustained drug delivery system as claimed in claim 17, wherein said effective agent is a neuroprotectant.

* * * * *